United States Patent [19]
Potter et al.

[11] Patent Number: 5,837,194
[45] Date of Patent: Nov. 17, 1998

[54] APPARATUS FOR MEASURING CHEMILUMINESCENCE OF MULTIPLE SAMPLES ON A CONTINUOUS MATRIX

[76] Inventors: Colin G. Potter, 12 Beech Road, Headington, Oxford OX3 7RR Oxyon, United Kingdom; Larry J. Anderson, Bldg. 7, Room B43, MS G17, Centers for Disease Control, Atlanta, Ga. 30333

[21] Appl. No.: 537,810
[22] PCT Filed: Apr. 25, 1994
[86] PCT No.: PCT/US94/04471
  § 371 Date: Jan. 11, 1996
  § 102(e) Date: Jan. 11, 1996
[87] PCT Pub. No.: WO94/25855
  PCT Pub. Date: Nov. 10, 1994

[30] Foreign Application Priority Data
Apr. 23, 1993 [FI] Finland ..................... 931858

[51] Int. Cl.$^6$ .................. G01N 21/01; G01N 33/53; G01N 21/00; C12Q 1/68
[52] U.S. Cl. .................. 422/52; 435/6; 435/7.1; 435/7.92; 435/287; 436/164; 436/516; 436/518; 436/807
[58] Field of Search ................. 435/6, 287, 7.1, 435/7.92; 422/52; 436/164, 516, 518, 807

[56] References Cited

U.S. PATENT DOCUMENTS

| | | | |
|---|---|---|---|
| 4,283,490 | 8/1981 | Plakas | 435/8 |
| 4,298,796 | 11/1981 | Warner et al. | 250/328 |
| 5,294,795 | 3/1994 | Lehtinen et al. | 250/328 |
| 5,306,617 | 4/1994 | Uchida et al. | 435/6 |

*Primary Examiner*—W. Gary Jones
*Assistant Examiner*—Paul B. Tran
*Attorney, Agent, or Firm*—Kubovcik & Kubovcik

[57] ABSTRACT

A method and apparatus for performing a chemiluminescent assay are disclosed. A test sample or multiple test samples is or are deposited on a supporting matrix and chemiluminescence of the sample(s) is effectuated. Low energy chemiluminescence emitted during chemiluminescence is removed by a light attenuation optical filter. Chemiluminescence is detected from the filtered light using a light detector means and chemiluminescence is counted using a chemiluminescence counter coupled to the light detector means.

13 Claims, 11 Drawing Sheets

FIG. 11 ously-disposed photo-multiplier tubes must both detect
APPARATUS FOR MEASURING CHEMILUMINESCENCE OF MULTIPLE SAMPLES ON A CONTINUOUS MATRIX This application is filed under 35 USC 371 as the national stage of International Application PCT/US94/04471, filed Apr. 25, 1994.

FIELD OF THE INVENTION

This invention relates to a method of and apparatus for detecting chemiluminescence from a multiplicity of discrete samples arrayed on a surface in a defined format, such as a matrix.

BACKGROUND OF THE INVENTION

Various assay systems including immunoassays, receptor-ligand assays and probe hybridization are known for detecting desired chemical and biological information. For example, probe hybridization is used to detect specific nucleic acid sequences in a sample and involves the formation of a base-paired duplex from two single stranded nucleic acid molecules. With probe hybridization, in the dot-blot technique, the nucleic acid may be bound to a flat matrix such as a nylon membrane or nitrocellulose paper and detected by reacting it against a labelled nucleic acid that is complementary to a portion of the bound nucleic acid. Such labeled nucleic acid probes can be used to detect target sequences by hybridization to DNA or RNA.

The most commonly used label in assay systems for nucleic acids is radioactive phosphorus ($^{32}P$). Although radioactive labels are widely used in research laboratories, well-known problems with such radioactive labels—e.g., short half-life, safety and disposal problems, and the necessity to perform long auto-radiographic exposures for detection—generally preclude their use in clinical and other settings. This has resulted in the development of a number of non-radioactive labels, and associated detection methods. For example, probes labelled with fluorescein and with enzymes such as alkaline phosphatase and peroxidase are in common use. However, utilization of these labels has been limited by their lack of sensitivity compared with $^{32}P$.

Figure 1:
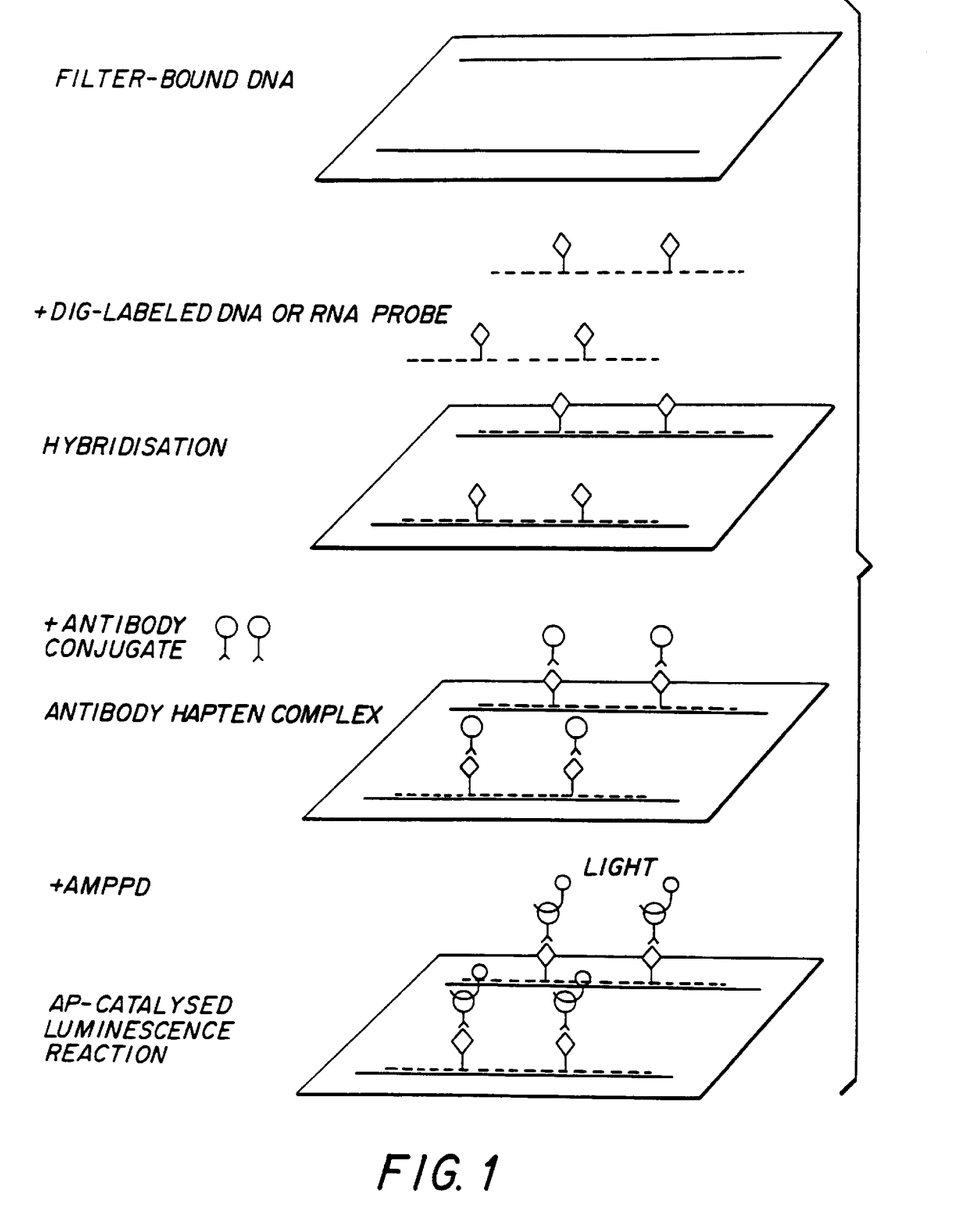
FIG. 1 shows the hybridization and chemiluminescence process for the DIG system from Boehringer Mannheim.

Recently, non-radioactive labeling and detection systems for nucleic acids have been introduced based on detection of chemiluminescence which have sensitivities closer to that of $^{32}P$. Noteworthy among such chemiluminescence detection systems are: Enhanced Chemiluminescence (ECL) from Amersham International; Flash™ from Stratagene Cloning Systems; and Digoxygenin (DIG) from Boehringer Mannheim. FIG. 1 illustrates the hybridization and chemiluminescence process for the DIG system.

As is well known, chemiluminescence is a form of luminescence resulting from chemical reactions. (The reaction leading to light emission in bioluminescence is similar but generally requires either oxygen or hydrogen peroxide as a reactant.) With either chemiluminescence or bioluminescence, light is emitted in the form of single photons. Other forms of luminescence are generally distinguished by the form of stimulus for the light emission, e.g., fluorescence, where light is emitted in response to an external stimuli, such as light, and scintillation, where multiple photons are produced by a single event, such as an electron emitted from a decaying radioactive atom.

Currently, in probe hybridization assays, chemiluminescence is most often detected by exposing the matrix containing the sample plus hybridized labelled probe to X-ray film for a period of 10 min. to several hours, depending on the required sensitivity. Such autoradiography does not permit direct quantification of chemiluminescence, but densitometry may be applied to the x-ray film to obtain a quantitative measure of limited range.

An alternative approach is to use photodetectors to read the chemiluminescence. A common instrument having such detectors is the liquid scintillation counter. Such counters normally operate in a coincidence mode, in which a pair of oppositely disposed photo-multiplier tubes must both detect an event for the event to be registered as a multi-photon event characteristic of scintillation. However, by turning off one of such oppositely-disposed photo-multiplier tubes, the machine can count single photon events. In this manner, a liquid scintillation counter could be used to detect and quantify chemiluminescence, essentially through a measure of the number of photons emitted over a defined time interval.

For DNA and other work, chemiluminescent samples may be disposed as sample spots bound to a membrane, such as nylon, that could be separated by cutting them out and placing in scintillation vials for counting. This separation step is a serious disadvantage, precluding application of the method to a large number of samples. While detection of chemiluminescence and other light emission from multi-welled plate assays are well known, special instrumentation is necessary and such instruments measure the electric current produced in a photodetector by the incident chemiluminescent light. Alternatively, it is proposed here to quantify the chemiluminescence from samples, preferably, multiple samples on an intact matrix produced by, for example, digoxygenin-labelled DNA probes, using a flat-bed multi-detector scintillation counter with one set of oppositely-disposed photo-multiplier (PM) tubes disabled. (Such a flat-bed scintillation counter is described in U.S. Pat. No. 4,298,796 and UK Patent No. 1 586 966, issued to Warner & Potter.) With this technique, the limitation that separate samples must be placed in separate scintillation vials for chemiluminescent counting is avoided.

SUMMARY OF THE INVENTION

An object of the present invention is an improved method of counting chemiluminescence using photodetectors.

A principal object of the present invention is a method of counting multiple chemiluminescent samples that are not separated but are arranged as an array on a continuous support matrix.

In order to accomplish the above, a method and apparatus are proposed for assay systems that use chemiluminescence as a detection means, e.g., systems for detecting specific nucleic acid sequences and other macromolecules using a non-radioactively labeled ligand or probe hybridization to produce chemiluminescence and wherein samples to be tested are not separated but are instead arranged as an array on a continuous matrix and detection of such chemiluminescence is accomplished by photodetector-based instrumentation. As a further refinement of the disclosed invention, optical filters having transmission characteristics determined in accordance with the luminance to be detected are disposed between the sample and the photodetector. The method and apparatus according to the present invention also can be used for double chemiluminescent labelling or radioactive and chemiluminescent labelling as will be described.

DETAILED DESCRIPTION OF THE INVENTION

As a test bed for development of the disclosed invention, oligonucleotide probes were used for hybridization to samples derived from PCR (Polymerase Chain Reaction, Cetus Corp.) that were spotted on a nylon transfer membrane (Boehringer) and hybridized according to the method recommended by Boehringer (See Boehringer Mannheim Biochemica technical bulletins entitled *DIG Oligonucleotide 3'-End Labeling Kit* (Cat. No. 1362372) and *DIG Luminescent Detection Kit* (Cat. No.13653514)). The chemiluminescent reagent AMPPD® was added, which acts as a substrate for alkaline phosphatase conjugated to a FAB antibody that recognizes digoxin-labelled oligonucleotide probes (FIG. 1). The nylon filters were wrapped, while still wet, in plastic film (e.g., Saran wrap) and placed between the perforated plates of a cassette and thence placed in position for counting by a multidetector counter.

One of the problems which has been associated with the attempted use of a multi-channel scintillation counter to count chemiluminescence is that the light output needed for maximum signal-to-noise ratio is so great that some counting registers in the multichannel analyzer of the counter, particularly those used for counting at the lowest end of the pulse height spectrum, become filled almost instantly. For a multi-detector system this resulted in very few counts detected for some samples and, although it gives high count rates, the precision could be very poor.

This problem can be explained by the fact that it is thought that chemiluminescence is often emitted in bursts of light, when considered on a microsecond basis, giving rise to high count rates of low amplitude pulses in the photomultiplier (PM) tube. For the multiple heads of such a multi-detector system, when attempting to count at a very high rate, one of the PM tubes will by chance receive such a high total count in one of the registers of its multichannel analyzer that it must stop counting, which in turn causes the other PM tubes to also turn off. The counting time might have been only a few microseconds, such that when the count rate per minute is calculated, it may be very high. In another PM tube, however, the sample being counted may have been relatively inactive during the short interval of the count, and it is possible that only one or two events may have been registered. When calculated, this may still give what appears to be a high count rate but with a very large associated error (calculated conventionally as the square root of the total number of events counted from that sample).

Figure 2A:
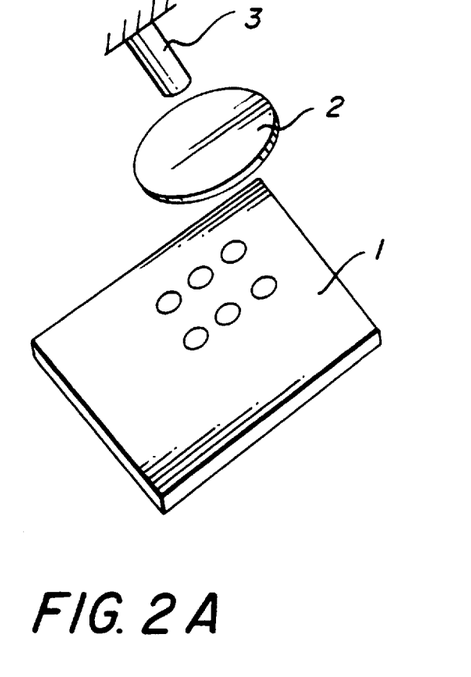
FIGS. 2A and 2B show an embodiment of the system of the invention
Figure 2B:
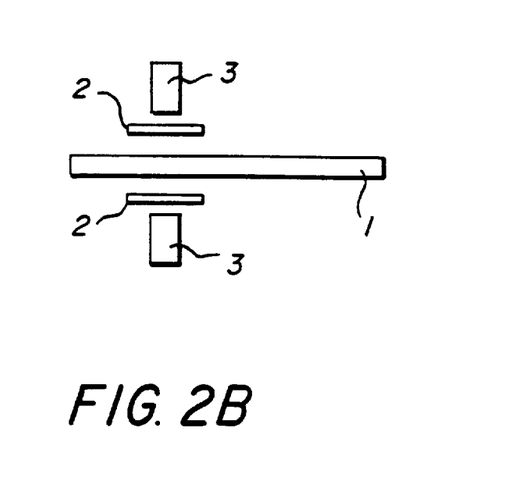

With the invention, this problem has been solved by placing an optical filtering means, which may be a neutral density or colored filter, between the nylon and the PM tubes. A representation of the system of the invention appears in FIGS. 2A and 2B. As will be seen in that figure, a flat-bed scanning system is represented having a bed 1 and photodetector scanning means 3. The sample matrix under consideration will be placed on the bed 1 and chemiluminescent emissions from the sample will be detected by scanning means 3. The scanning means 3 may be located in a plurality of locations, including opposite sides of bed 3, as illustrated in FIG. 2B, as well as in multiple locations above or below bed 3. As a key element of this invention, optical filter means 2 is disposed between each scanning means 3 and the sample being observed by that scanning means.

Figure 4A:
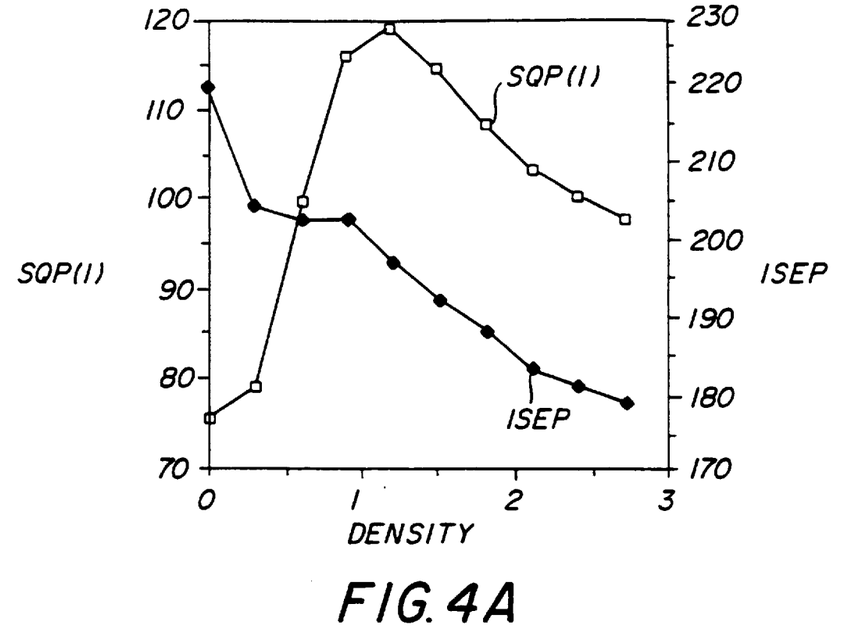
FIG. 4A shows the relationship between count rate and filter density for neutral density filtration disposed between the sample and the PM tube.
Figure 4B:
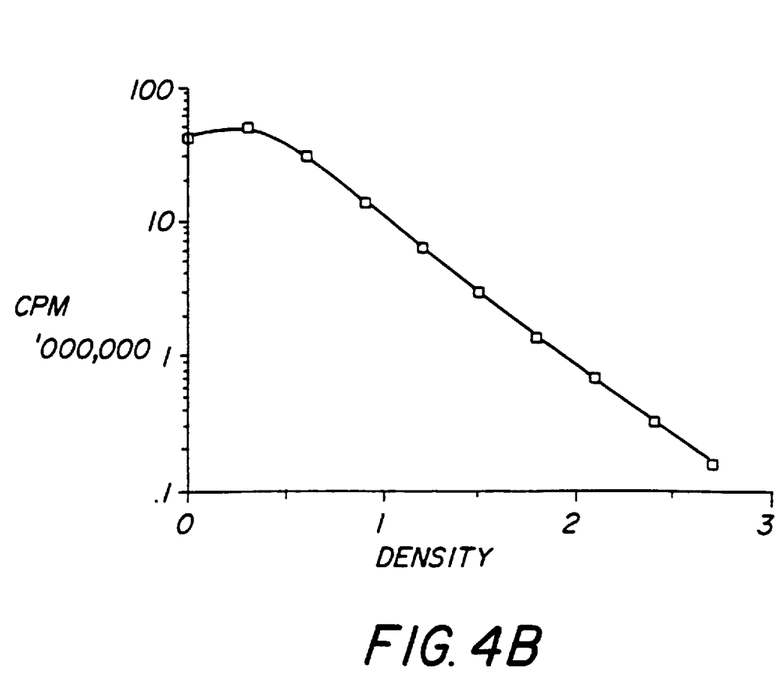
FIG. 4B shows the relationship between mean pulse height channel, SQP(I), and filter density.

As shown in FIG. 4B, disposition of such a filter, using a neutral density filter, caused the count rate to initially increase slightly and then to decrease as filter density increased. This relationship can be explained by the fact that, without the neutral density filter in place, the coincidence of events results in an apparent merger of some of the pulses and thus will cause the counter to record a count rate less than the actual number of events. This is particularly the case where a large number of low energy events occur. These lower energy events are preferentially filtered out and the neutral density filter operates to achieve this result, thereby producing a unimodal pulse-height energy spectrum and the desired improvement in counting effectiveness.

Figure 3A:
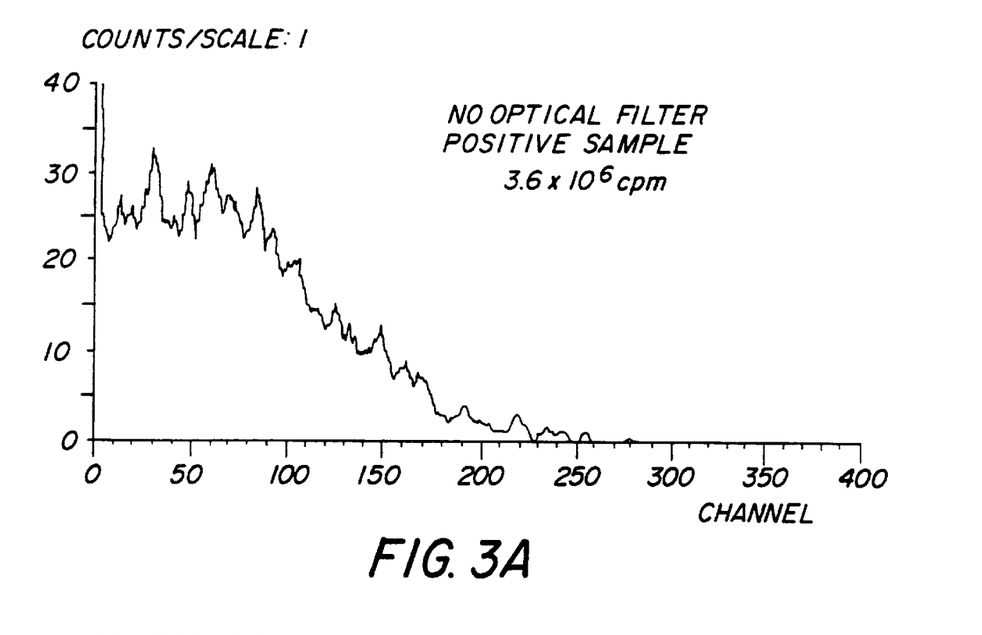
FIGS. 3A and 3B show sample pulse height spectrum for positive and background samples counted without filtration.
Figure 3B:
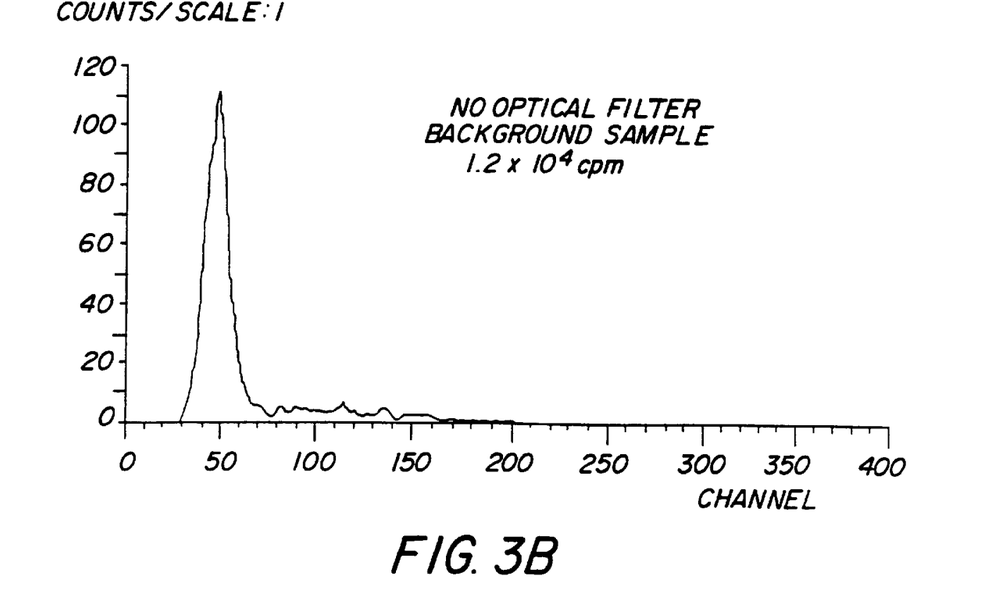
Figure 3C:
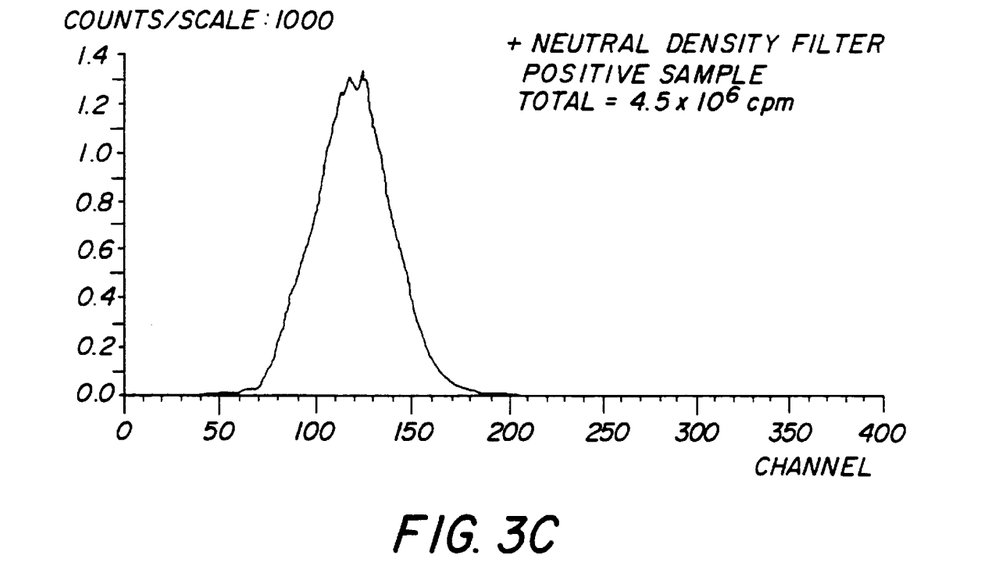
FIGS. 3C and 3D show noise pulse height spectrum for positive and background samples counted with filtration.
Figure 3D:
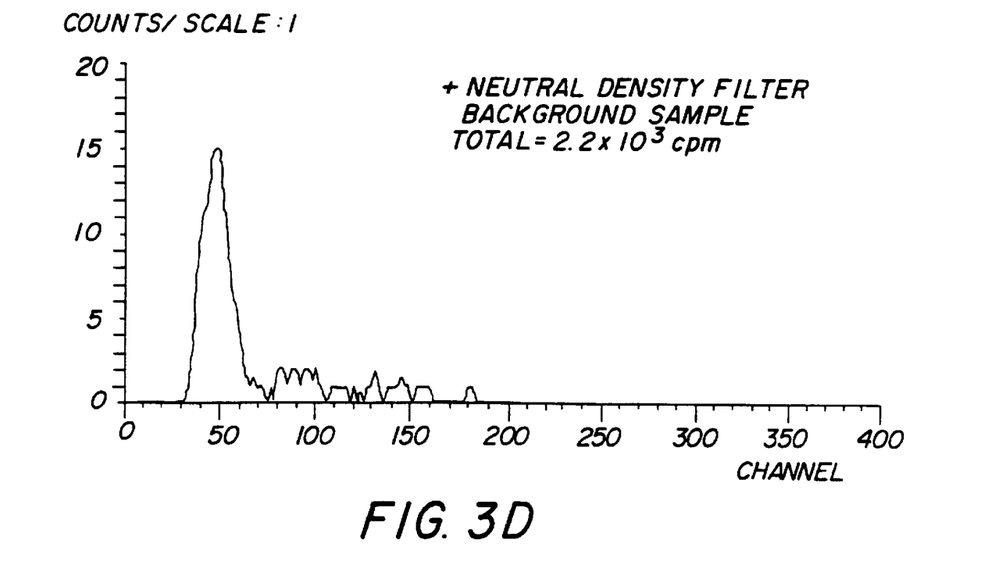

As will be seen in FIGS. 3A and 3C the pulse height spectrum changes with decreasing count rate. Without the filters a broad peak occurs in the pulse height spectrum, as seen in FIG. 3A. With the filters that peak becomes much sharper (FIG. 3C) and therefore the pulse height channels window can be reduced to channels 75–250 with the instrumentation of choice for this embodiment, as compared with channels 5–320 when set in coincidence mode for scintillation counting of tritium with this instrumentation. By comparing FIGS. 3B and 3D, it can be seen that the invention results in a reduction of the PM tube noise counts to about 1000/min for quartz photo-multiplier tubes and about 4000/min for a conventional tube machine and also results in an improved signal-to-noise ratio. In the described embodiment, chemiluminescence of both background signals were well above the instrumentation background levels and adequate precision was easily obtained with 10–30 second counting time.

FIG. 4B illustrates that the mean pulse height channel, or SQP(I), will increase to a maximum as the filter density is increased and then will be reduced if the density is increased further. Thus by looking at the position of the peak of the SQP(I) curve of FIG. 4A, one can choose a neutral density filter that gives a maximum mean energy level. In the described embodiment of the invention, a density of 1.2 density units was found to be optimum. However, a range of up to 1.8 density units was found to produce satisfactory results, especially where high pulse rates could result in reduced count rate due to merging of pulses.

Colored filters were also found to be effective at reducing count rate, yellow filters being more effective than blue for the same density, as would be expected from the well-known increased sensitivity of PM tube cathodes at the blue end of the spectrum. The signals also persisted at room temperature for several days. The ECL technique and the Flash™ chemiluminescent systems may be equally usable although they would be expected to produce light for a shorter time.

Figure 5A:
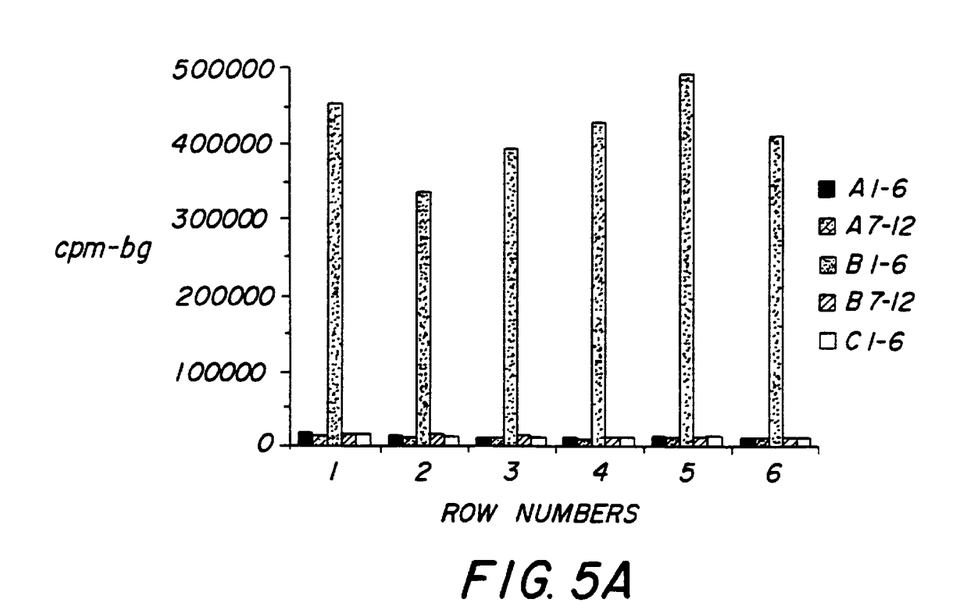
FIGS. 5A–D show the effect of cross-talk using the method of the invention as measured over a 5-day period.
Figure 5B:
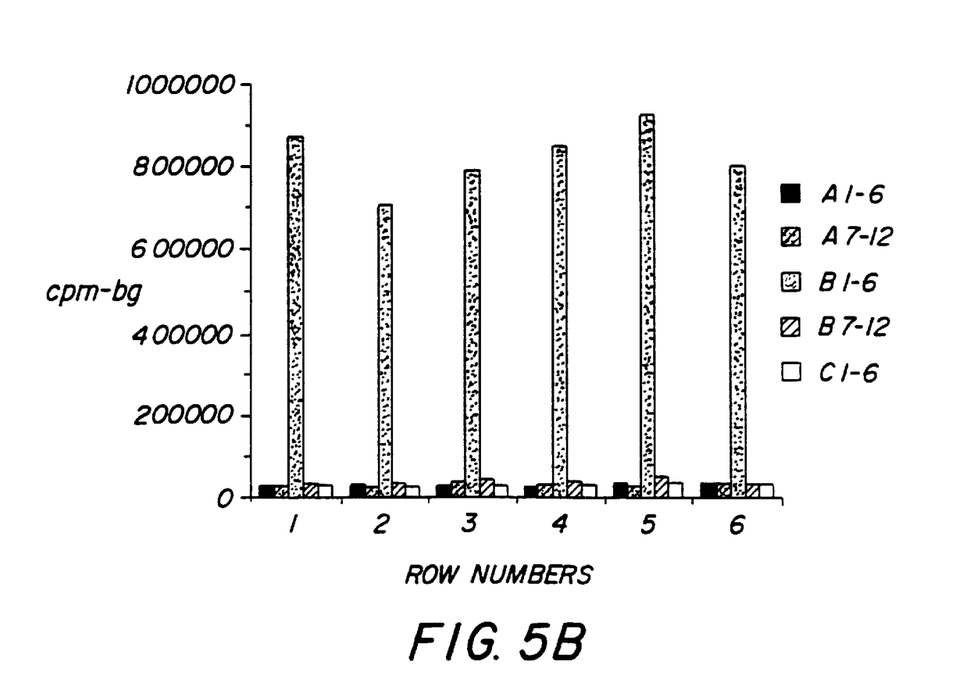
Figure 5C:
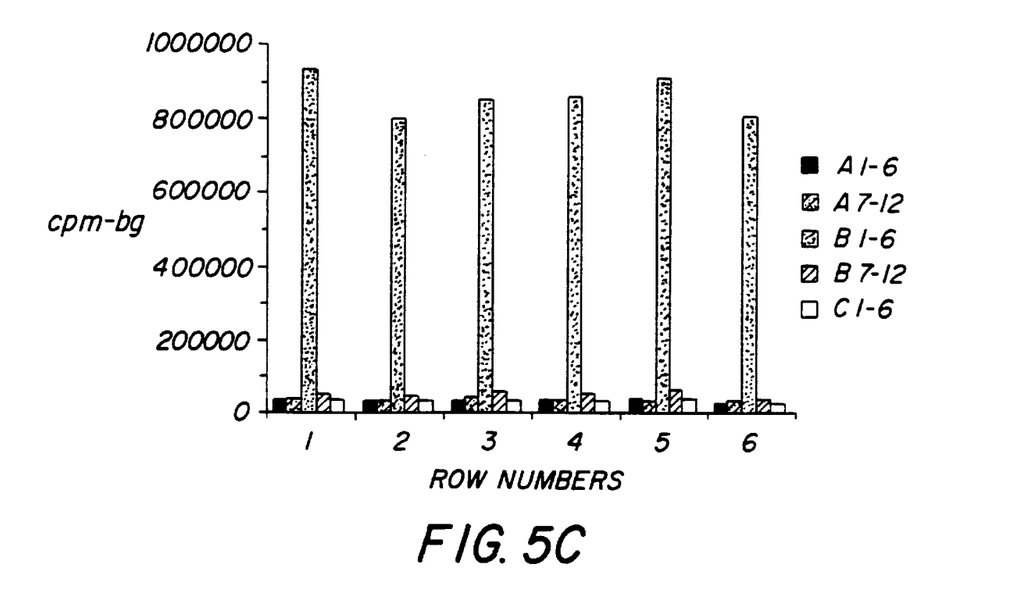
Figure 5D:
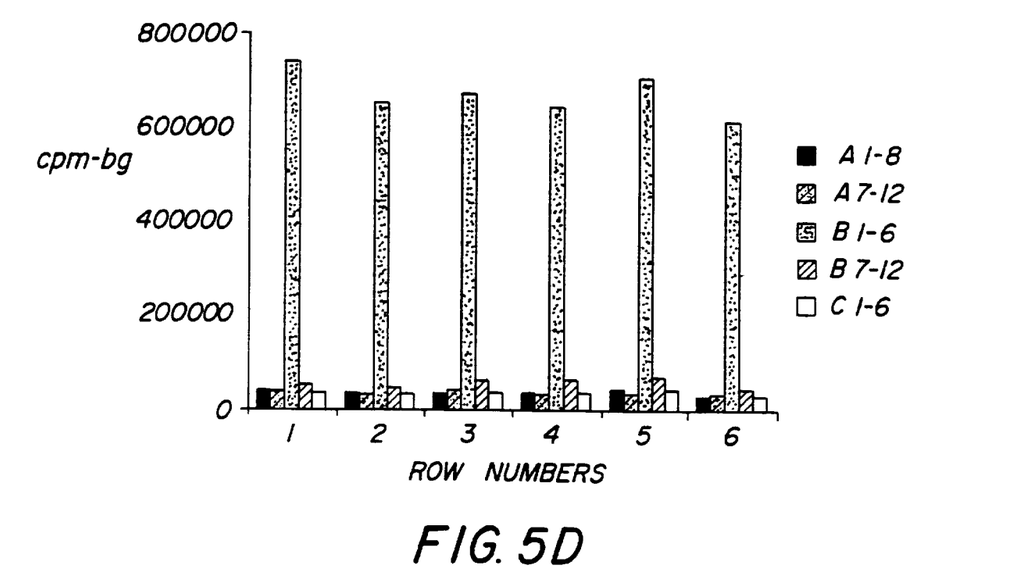

In the disclosed invention, cross talk—defined as the counts detected in an adjacent blank sample area to an active sample—was not detected for chemiluminescent samples consisting of six test samples in a row which were measured together with the two blank rows on either side (FIG. 5A) with a large format Wallac Betaplate™ flat bed counter. With measurements made on days 2–5 (FIGS. 5B–D), some small amount of diffusion of sample or dissociation of probe gave rise to a low level of counts in adjacent samples areas although this was not cross talk. Cross talk was similarly not detected using a small 8×12 microtitre format in the Wallac Microbeta™ scintillation counter, also in non-coincident mode. In contrast, cross talk can be a serious problem in prior-art liquid flat-bed scintillation counting of filters, requiring, for example, the disposition of a black grid for absorption of the laterally emitted light, such as disclosed in U.S. Pat. No. 4,728,792 issued to Warner and Potter.

Figure 6:
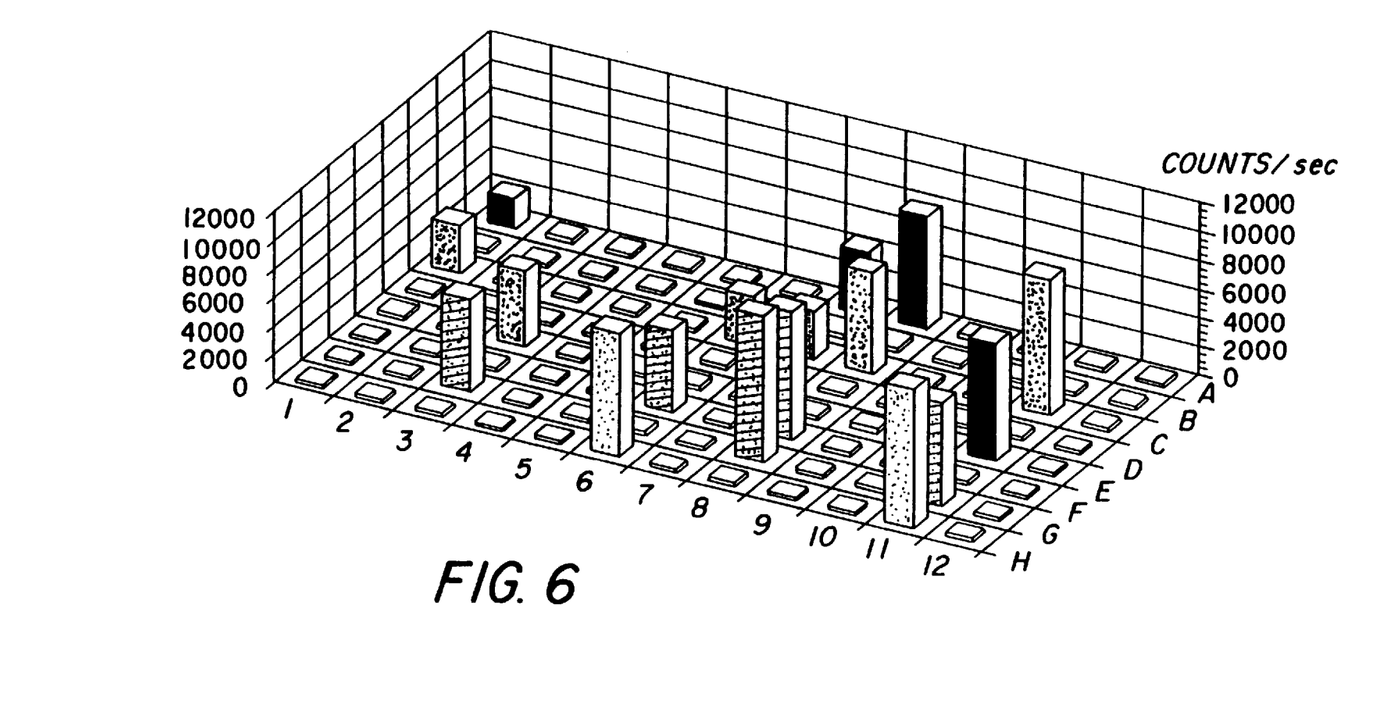
FIG. 6 shows typical results for the method of the invention using a 6-tube flat bed counter designed for 96 well plates or microtitration format filter matrices.

With the present invention, however, the chemiluminescent samples can be counted for 10–30 seconds with good precision, so that a 96 sample plate would take no more than 10 minutes to count on a 6-tube flat-bed counter with 30 sec/sample counting times. Typical results are shown in FIG. 6 where 5 μL DNA solution aliquots were spotted on nylon—the samples being derived from PCR amplification of cDNA produced by the action of reverse transcriptase on mRNA. As will be readily understood, this counting methodology represents a much shorter procedure and is more convenient than autoradiography where, however short the exposure time, the filter must be placed next to the film in a dark-room and later removed and processed. In addition, the novel methodology gives a direct quantitative measure of the hybridization reaction.

It should also be observed that autoradiography could be accomplished for these samples with exposure of 10 minutes–2 hours. By comparison, autoradiographic detection of probes labeled with $^{32}P$ will require exposure from overnight to several days. In addition, DNA dot blot samples labelled with $^{32}P$ may need up to 60 mins counting time.

Chemiluminescent samples detected according to the invention can also be used to detect bands in a series of tracks or lanes such as those produced by electrophoresis. And, the above described system can be used to scan the tracks in small increments thereby building up quantitative data to allow integration of counts for each band encountered during the scan. Samples arranged as a series of bands are scanned in one direction whereas samples arranged as spots whose positions are not known beforehand are scanned in two dimensions.

For machines with double photo-multiplier tubes normally used in coincidence for scintillation counting, it will be possible to use both tubes independently, one each to count photons from samples on each of two supporting matrices placed back-to-back with a light proof barrier between them. A six-tube flat-bed counter (such as the Wallac Betaplate™ or Microbeta™ counter) could then count 12 samples at the same time for even more rapid throughput of samples.

As a further embodiment of the invention, more than one chemiluminescent system can be employed simultaneously. For example, one nucleic acid probe could be labelled with digoxygenin and a second probe labeled with biotin. The labels could then be detected with an antibody (or streptavidin for biotin) conjugated with a different enzyme. The DIG system from Boehringer uses alkaline phosphatase with AMPPD and has a maximum light output at a wavelength of 477 nM, while the ECL system from Amersham uses horseradish peroxidase with its substrate of dioxetane and produces light at a maximum output at a wavelength of 428 nM. As is true in this example case, the two (or more) systems must not interact chemically.

In this double-labeling embodiment, the difference in color spectrum output can be detected by the use of appropriate optical filters, successively interposed between the sample and photo-multipliers. Of course, the spectral windows of the filters for the top and bottom PM tubes must be chosen to pass the light at peak wavelength for the output of each assay. In addition, neutral density filters will reduce the output to levels suitable for counting.

Figure 7:
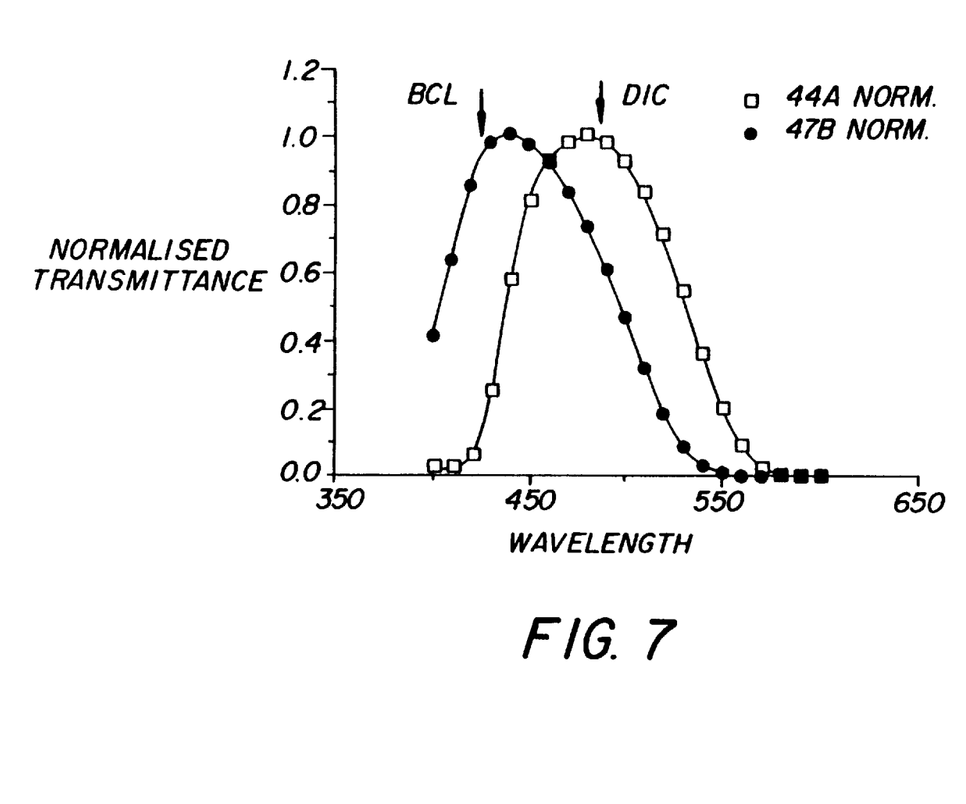
FIG. 7 illustrates normalized transmittance characteristics for colored filters usable for the double labeling embodiment of the invention.
Figure 8:
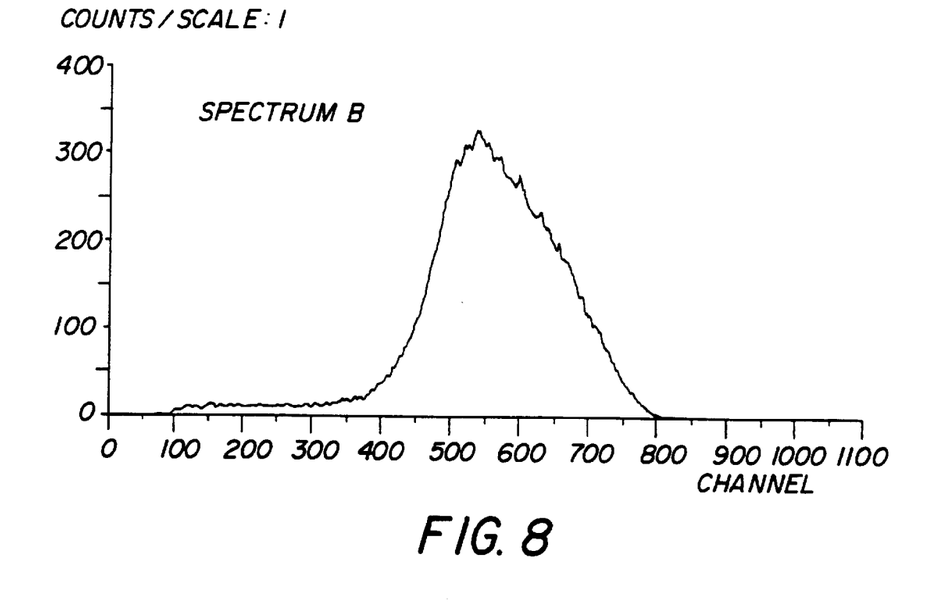
FIGS. 8 and 9 show pulse characteristics for $^{32}P$ labeled probes in a dual radioactive/chemiluminescent labeling mode.

In a preferred embodiment, filters 44A and 47B from the Tricolor Filter range from Eastman Kodak would be used. Normalized transmittance data for these two filters is shown in FIG. 7 to illustrate the displaced peaking characteristics of those filters as related to the spectral output of the DIG and ECL treated probe.

The ratio of outputs of one optical filter compared with the other filter for singly labelled standardization samples would permit determination of calibration data. For mixed samples the ratio of outputs could be used in conjunction with the calibration data to calculate each probe's contribution to the count rate. It will be appreciated that this method represents an improvement compared with parallel sets of samples being tested successively. For example, one can test the exact same sample for two different sequences or types of molecule, making it possible, among other things, to include an internal control.

As a further refinement of this double-labeling embodiment, a pair of photo-multipliers, one on each side of the sample, can be used with different optical filters suitable for the respective light output. The ratio of the simultaneous count rates so obtained would allow double label counting with a high throughput.

Finally, if a pair of photo-multiplier tubes are used with one or two chemiluminescent systems being detected, it will also be possible to count samples labelled with radioactivity by recording the coincident events from both tubes—although the chemiluminescence must be low enough for coincident single photon events to be rare compared with radioactive decay of the sample. Even if small rates of chemiluminescent coincidence are detected, is tends to have low pulse height, whereas for isotopes such as $^{35}S$ and $^{32}P$ used from DNA probe labelling, the mean pulse height is much higher than chemiluminescence and can be separated by appropriate setting of the pulse height window.

For dual radioactive/chemiluminescent labelling there must be minimal interaction under the different counting conditions required for the different measurements, or at least there should be a means of correction. To test the effectiveness of the invention in satisfying this criteria, a dilution series of chemiluminescent samples were first counted under conditions suitable for chemiluminescence and then samples with radioactive phosphorus-32, either alone or spotted on top of the chemiluminescent samples, were counted. For the radioactive measurement of phosphorus, the water-wet nylon filter wrapped in plastic film was sandwiched between two glass fibre filters each being within a thin plastic bag and permeated with scintillant. This method of measuring $^{32}$P is described by C. G. Potter and S. Le Jeune, "Quantitative analysis of nucleic acid dot blots using the Betaplate flat-bed scintillation counter," (1991) Technique, 3, 117–121. For this application the Wallac Microbeta counter was set up for filter counting, including use of a neutral density filter of 1.8 density units—specifically our filter was comprised of 2 Lee 211 filters each of 0.9 density units. The pulse height spectrum for $^{32}$P shown in FIG. 7 is similar to that shown by Potter and Le Jeune using their larger format Betaplate counter.

Table 1 shows that non-coincident count rates are decreased by the 1.8 density unit neutral density filters, although addition of glass fibre/scintillant filters increased the count rates slightly. This is believed to be due to better reflection of chemiluminescent photons by the backing glass fibre filter compared with the (dark) photo-multiplier assembly. The total of randomly coincident counts ranged from 3.03% at 8,380 non-coincident counts to 13.4% of 269,150 cpm, varying with the count rate as expected. If the energy channels were restricted to those suitable for $^{32}$P (channels 201–900) in the instrumentation of choice, it was difficult to measure the counts, as they were less than 0.014% of the total non-coincident counts. Most coincidences were in channels 75–200. These channels are also used for the non-coincidence counting of chemiluminescence.

TABLE 1

Counts per minute above background of chemiluminescent and $^{32}$P labelled samples

| Chemiluminescent Samples - means | 1. (n = 3) | 2. (n = 4) | 3. (n = 4) |
|---|---|---|---|
| 1. No coincidence but with glass fibre filters + scintillant. Pulse height channels 75–200. | 559760 | 160090 | 20670 |
| 2. Same as 1 above but also with neutral density filter. | 269150 | 57780 | 8380 |
| 3. Same as 2 above but without glass fibre filter sandwich. | 236010 | 46090 | 8970 |
| 4. Same as 1 above but with coincidence (% of 1 above random coincidence) Channels 201–900 for $^{32}$P | a. 35900 (13.3) b. 11.5 (0.03) | 4798 (8.3) 7.5 (0.16) | 254 (3.0) 0.4 (0.15) |

| | |
|---|---|
| 5. $^{32}$P samples on nylon (n = 3) with glass fibre filter sandwich only, plus coincidence | mean = 692 ± 27 S. D. |
| 6. Same as 5 above but channels 75–200 | mean = 0.0 ± 0.0 S. D. |
| 7. $^{32}$P samples (n = 8) on nylon with chemiluminescence-emitting background | mean = 729 ± 73 S. D. |
| 8. Same as 7 above but channels 75–200 | mean = 1218 ± 1144 S. D. |

Figure 9:
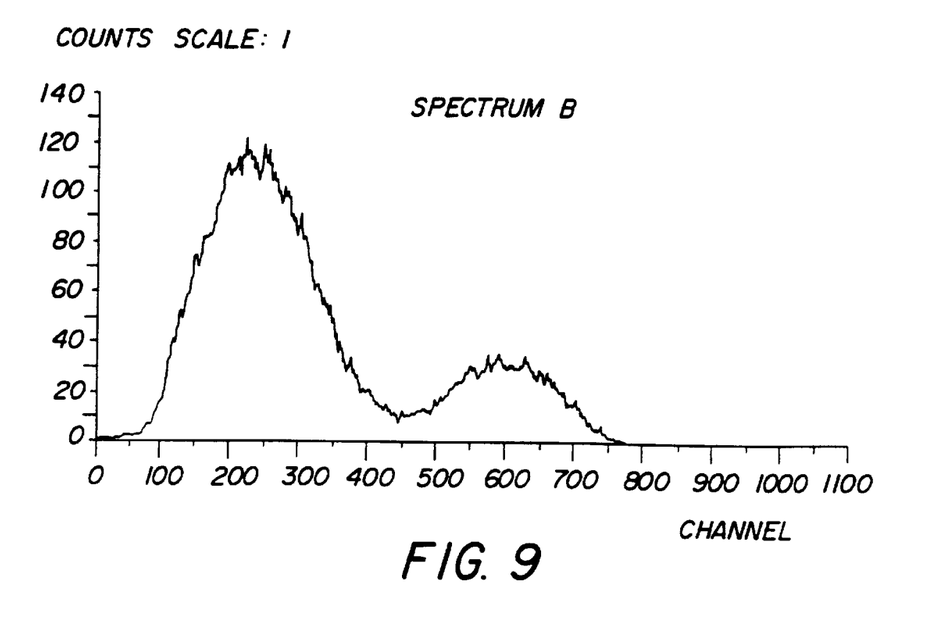

Three samples consisting of DNA probes labelled with $^{32}$P were spotted onto nylon in amounts typical for hybridization assays as shown in Table 1. Very few counts were registered in channels 75–200 when these samples were counted in the non-coincidence long-pulse mode (Spectrum A on the machine), suitable for chemiluminescence. Because the neutral density filter cut down the light output, the pulse-height spectra were lower and bimodal as illustrated in FIG. 9. Overall counting efficiency for $^{32}$P was reduced by about 60% in a subsequent test with higher activity samples because of the presence of the neutral density filter.

Samples already emitting chemiluminescence and previously measured were then spotted with $^{32}$P radioactive probe at a low activity typical of hybridization samples and recounted. The instrument was then set to measure shorter pulses (Spectrum B on the machine), suitable for $^{32}$P, and it was found that there was some interference of the random coincidences of the chemiluminescence with the phosphorus measured in channels 201–900. This spillover varied with chemiluminescent count rate as described above and this was more reliably determined from the long-pulse mode because the shorter pulse length mode gave rise to very high count rates (5–70 million cpm) that were difficult to manage as counting times were sometimes down to 0.03 sec.

The interference could be reduced by choosing a higher setting for the lower discriminator gate. For 8 samples placed on background chemiluminescence with 1000 cpm in channels 75–200 (Sample 7 of Table 1), there was no apparent interference as the mean cpm of the 8 samples was not significantly different from the mean of the three spotted on nylon.

Figure 10:
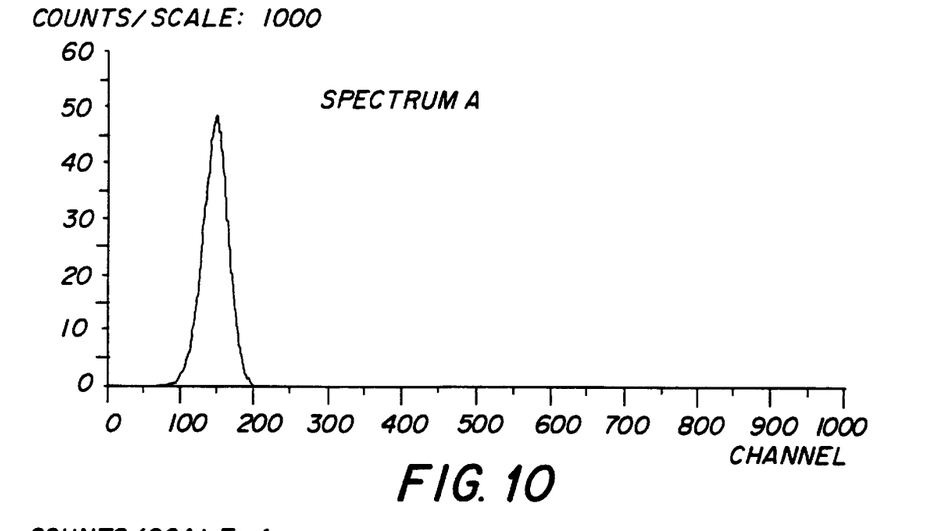
FIGS. 10 and 11 show pulse characteristics for chemiluminescent labeled probes in a dual radioactive/chemiluminescent labeling mode.
Figure 11:
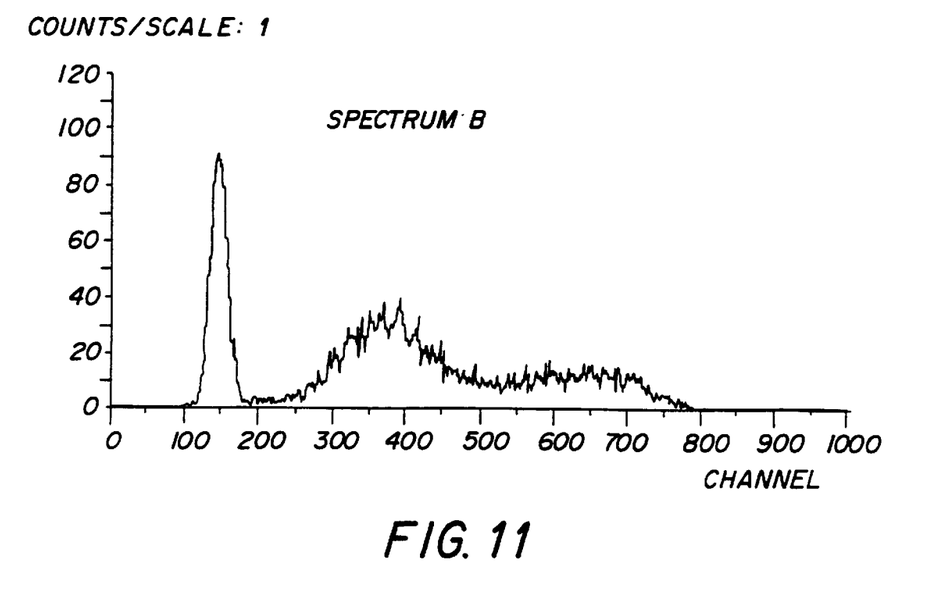

FIG. 10 shows the long-pulse non-coincidence pulse height spectrum for digoxigenin/AMPPD chemiluminescence alone. FIG. 11 shows coincident counting of shorter pulses (80–100 nS) for $^{32}$P together with chemiluminescence. As before, the sample bearing filter was set up between a sandwich of glass fibre filters bagged with scintillant and neutral density filters of density 1.8 placed between the filter assembly and the active photo-multiplier tubes.

Thus, it is seen that a scintillant containing sandwich with neutral density filters can be used to measure simultaneously (or in succession): (1) chemiluminescence by short pulse counting with low energy pulse height discrimination and (2) radioactivity by counting shorter pulse lengths with higher pulse height discrimination. It may also be necessary to use a series of samples having different chemluminescent activities to provide correction values for random coincidence spillover into coincidence counting.

Although the invention has been described in conjunction with a probe hybridization assay using a specific chemiluminescent system, it is to be understood that the invention can be used for performing any assay where chemiluminescence is used as a detection means. Such assays include immunoassays, receptor-ligand assays and the like. Furthermore, the invention can be used in conjunction with any kinown system for producing chemiluminescence.

The terminology "continuous support" and "supporting matrix" used herein are intended to include microtitration format filter matrices, such as a 96 well microtitration plate.

Herein, we have described a method of and apparatus for the very raped quantification of chemiluminescent samples, that is much quicker than autoradiography or any known isotope labelling detection technique. This unique invention may become very important in high throughput research projects and diagnosis. Although the present embodiment of the invention has been described in detail, it should be understood that various changes, alterations and substitutions can be made therein without departing from the spirit and scope of the invention as defined by the appended claims.

What is claimed is:

1. An apparatus for performing a chemiluminescent assay on multiple test samples deposited together on a continuous support, the continuous support containing a reactant that effectuates chemiluminescence of the multiple test samples, the apparatus comprising:

flat bed means for holding the multiple test samples deposited on the continuous support during the performance of the assay;

light detector means for detecting light emitted during chemiluminescence of the multiple test samples, said light detector means being disposed opposite said flat bed;

chemiluminescence counter means for counting chemiluminescence of the multiple test samples, said chemiluminescence counter means coupled to said light detector means; and filter means for filtering light emitted during chemiluminescence and passing the light to said light detector means, said filter means being disposed in the optical path between said flat bed means and said light detector means, wherein said filter means is a light attenuation optical filter that precludes low energy chemiluminescence from being detectable by said light detector means.

2. The apparatus for performing a chemiluminescent assay as recited in claim 1, wherein said filter means is a neutral density filter or a coloured filter.

3. The apparatus for performing a chemiluminescent assay as recited in claim 1, wherein the multiple samples are disposed in a multiwell plate.

4. The apparatus for performing a chemiluminescent assay as recited in claim 1, wherein said continuous support comprises two supports placed back-to-back with a light proof barrier between them.

5. The apparatus for performing a chemiluminescent assay as recited in claim 2, wherein the density of said neutral density filter is from about 1.2 to about 1.8 density units.

6. The apparatus for performing a chemiluminescent assay as recited in claim 1, wherein said light detector means is at least one photomultiplier tube of a multi-channel analyzer, and said chemiluminescence counter is a plurality of counter registers for storing the number of chemiluminescent events detected.

7. The apparatus for performing a chemiluminescent assay as recited in claim 1, wherein the multiple chemiluminescent samples are bound to a continuous support in the form of an M x N array, wherein M and N are positive integers.

8. The apparatus of claim 7 wherein said samples are nucleic acid samples and said reactant is at least one labelled nucleic acid probe.

9. The apparatus for performing a chemiluminescent assay as recited in claim 8, wherein the reactant comprises two labelled nucleic acid probes.

10. The apparatus for performing a chemiluminescent assay as recited in claim 9, wherein said two labelled nucleic acid probes are two chemiluminescent probes.

11. The apparatus for performing a chemiluminescent assay as recited in claim 9, wherein said two labelled nucleic acid probes comprise a chemiluminescent probe and a radioactive probe.

12. The apparatus for performing a chemiluminescent assay as recited in claim 11, where in said two labelled nucleic acid probes are detected by a pair of a combination of a photomultiplier and an optical filter, the combinations being disposed on opposite sides of the sample and the optical filters being different.

13. The apparatus for performing a chemiluminescent assay as recited in claim 8, wherein said reactant includes a labelled digoxigenin nucleic acid probe and a labelled biotin probe, thereby allowing the assay to detect simultaneous different sequences from the same multiple test samples.

* * * * *